United States Patent [19]

Mauermann et al.

[11] Patent Number: 5,132,264
[45] Date of Patent: Jul. 21, 1992

[54] CONCENTRATED WATER SOLUBLE ORGANIC LANTHANIDE SALTS

[76] Inventors: Heiko Mauermann, 38 Hartwell St., New Brunswick, N.J. 08901; Nicholas A. Sullo, 15 Seaview Ter., Guilford, Conn. 06437

[21] Appl. No.: 723,871

[22] Filed: Jul. 1, 1991

[51] Int. Cl.⁵ .............................................. B01J 31/12
[52] U.S. Cl. .................................................. 502/170
[58] Field of Search ........................................ 502/170

[56] References Cited

U.S. PATENT DOCUMENTS 3,867,312  2/1975  Stephens ............................ 502/302

*Primary Examiner*—Patrick P. Garvin
*Assistant Examiner*—Brent M. Peebles
*Attorney, Agent, or Firm*—John A. Shedden

[57] ABSTRACT

The instant invention relates to concentrated water soluble organic salts of the lanthanides, particularly the cerium salts which are useful in the production of exhaust emission reduction catalysts. The preferred compositions comprise cerium acetate with gluconic acid and excess acetic acid.

12 Claims, 2 Drawing Sheets

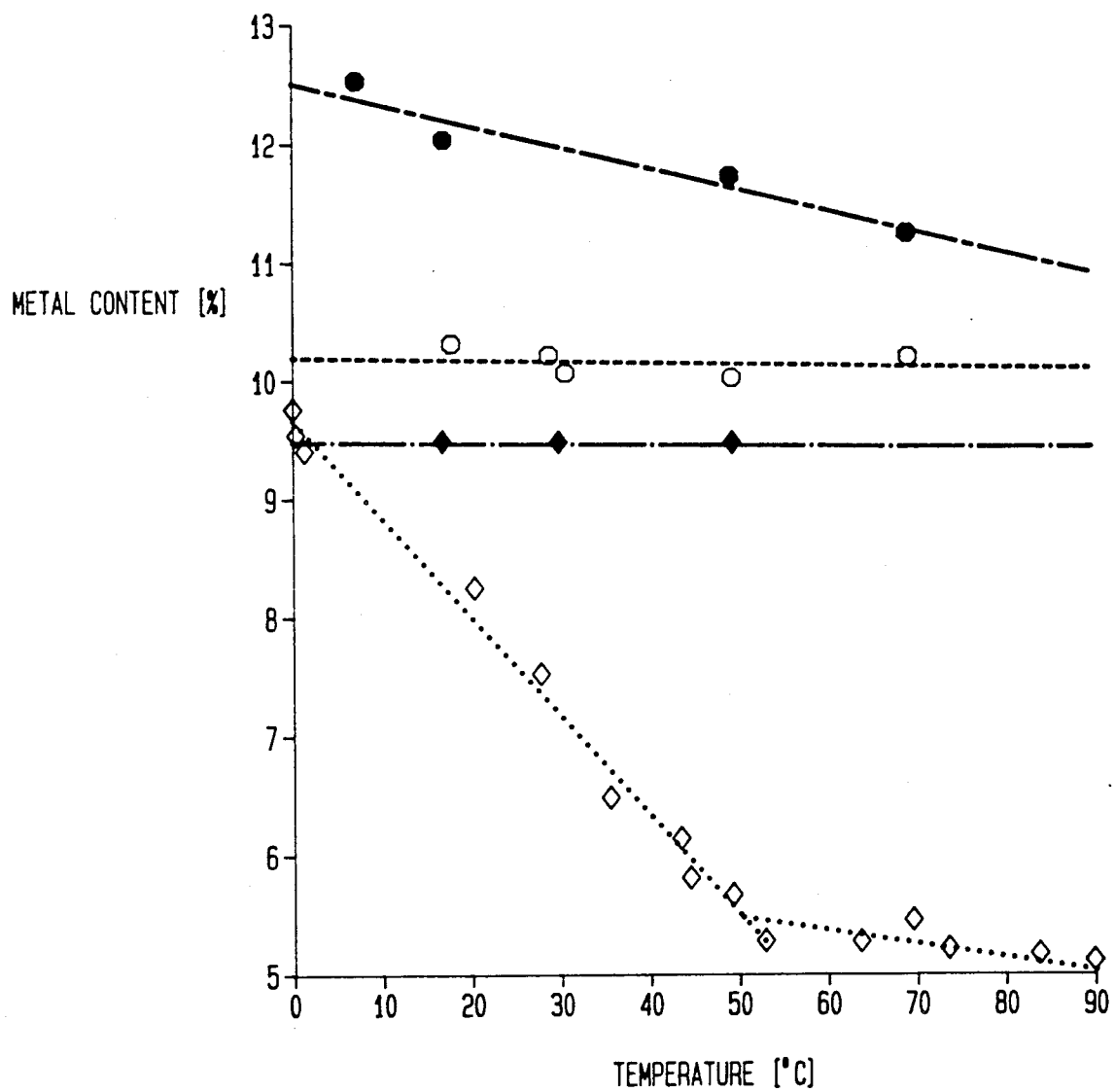

CONCENTRATED WATER SOLUBLE ORGANIC LANTHANIDE SALTS

BACKGROUND OF THE INVENTION

1. Field of the Invention

The present invention relates to low viscosity, concentrated water soluble organic salts of the lanthanides; methods for their preparations; and use. More particularly, this invention relates to the preparation of low viscosity, concentrated aqueous solutions of organic salts of cerium which have particular utility in the preparation of pollution reduction catalysts.

2. Description of the Prior Art

Multilayer catalysts that have been universally accepted in the catalytic converters of the automobile industry convert unburned hydrocarbons and carbon monoxide to carbon dioxide and water and additionally convert oxides of nitrogen to elemental nitrogen. These reactions occur at elevated temperatures, generally in the range of from about 100° C. to about 1300° C. The five major components of these vehicle exhaust catalyst usually comprise the substrate, the undercoat, stabilizers, metal promoters and platinum group metals. The support is primarily a low surface area structure which serves as a catalyst foundation by providing high rigidity and high strength. In the automotive industry, the support is generally a dense, honeycomb type structure with a thin, nonporous surface usually fabricated from cordierite. To this low surface area support is applied an undercoat having relatively high surface area which serves as an anchor or base for the catalytic entity forming the outermost surface of the catalytic composite.

Alternatively, the catalyst undercoat material per se may be compressed or extruded into various geometric forms and used directly to support the catalyst entity. Such a solid may be in a variety of forms including powders, granules, sheets, spheres, extradites, honeycombs, or monolith structures, cylinders or rings, saddle stars and the like. The highly porous undercoat is usually comprised of alumina. Rare earth oxide stabilizers, such as the lanthanide oxides, especially the cerium oxides, are often admixed with the alumina undercoat to maintain the high surface area at the elevated temperatures, such as 1000° C., that are often encountered during use.

U.S. Pat. No. 4,996,031 discloses a catalyst undercoat material comprising alumina and at least one lanthanide oxide which are co-precipitated from soluble salts. The lanthanide oxide is taught to be present in an amount of from about 1 to about 45 weight percent based on the total weight of the oxide and alumina present. Suitable aluminum salts disclosed include the nitrate, sulfate, chloride, acetate and oxalate. Suitable water soluble lanthanide salts disclosed include cerium nitrate, sulfate, chloride, acetate, lactate, propionate and butyrate; lanthanum nitrate, acetate and sulfate; praseodymium nitrate; and neodymium nitrate. It was noted that the nitrates were preferred because some of the other anions such as the sulfate can appear as an occluded ion in the precipitate, resulting in catalyst poisoning.

U.S. Pat. No. 4,868,149 discloses the use of a lanthanum laced cerium oxide/alumina slurry as a catalytic undercoat. One disclosed method for preparing the slurry involves impregnating the alumina with an aqueous solution containing a water soluble cerium compound and calcining the mixture in air at a temperature of from about 400° to 700° C. to realized well dispersed cerium oxide on the alumina. Another slurry preparation method disclosed involves co-precipitating or co-gelling a cerium compound with an aluminum compound and pyrolyzing same to achieve 5 to 50% by weight cerium oxide on the alumina.

Onto and into the porous undercoat is applied by impregnation, immersion, spraying or other means, the catalytic coating comprising oxidation catalysts from the precious metal groups and promoters.

These catalytic ingredients are well known in the art. Useful for this surface catalytic coating are certain of the base oxides of elements and mixtures thereof which are identified in Group 8 of the Periodic Table and which include the precious metals and individual elements such as manganese, chromium, and copper as their oxides or interreaction products. Particularly useful as surface catalytic components in the automobile emission reduction art are the precious metals, particularly platinum, palladium and rhodium.

Promoters, such as the lanthanide oxides, particularly cerium oxide (ceria) often provide dramatic increases in the catalytic efficiency of the precious metal catalysts under certain emission reduction conditions. For example, rhodium is extremely sensitive to deactivation at high temperatures under the lean operating conditions which can be encountered during extensive high speed driving. This deactivation is thought to be due to a strong rhodium-alumina interaction, which fixes rhodium in a high oxidation state which is difficult to reduce. This interaction can be reduced by the incorporation of ceria into the catalyst. Additionally, in the presence of water, significant increases in carbon monoxide conversion can be realized over precious metal catalysts in the presence of a cerium oxide additive.

U.S. Pat. No. 3,993,572 discloses catalyst compositions containing a platinum group, a rare earth metal oxide such as the cerium, samarium and praseodymium oxides, and an alumina component. The catalyst compositions may be prepared by co-precipitating the ingredients or by impregnating the alumina powder with, e.g., cerium salts.

U.S. Pat. Nos. 3,867,312 and 3,899,444 disclose another procedure which includes preparing an aqueous solution of water soluble decomposable salts of a rare earth metal and a water soluble aluminum salt, evaporating the free water from the solution and then heating the resultant mixture. A uniform mixture of salts is obtained; subsequently decomposed; and then cooled to produce a self-supporting catalytic entity.

The aforementioned catalysts are also used in the chemical industry or in abatement processes for the disposal of combustible or toxic materials including reducing pollutants in waste gases.

The above discussion and cited patents are generally representative of the state of the art. From these teachings, it can be seen that the water soluble organic salts of the lanthanides, especially the water soluble cerium salts are highly useful in the catalytic art. However, while the cerium acetate, propionate and lactate salts do not realize undesirable occludable anions that can negatively affect the activity of the final compositions nor produce environmentally unacceptable by-products under pyrolysis conditions, they have relatively low water solubilities. This low solubility in water results in the necessity of multiple steps to achieve the high lanthanide oxide loadings required by the above described catalytic art.

Furthermore, not only is it desirable to utilize water soluble organic lanthanide salts at high concentrations, but the concentrated solutions themselves must, of necessity, be of low viscosity to enable the solution to easily coat particles of the other catalyst components and/or to easily penetrate into the interstices such as the honeycomb structures, of the support or undercoat. Merely diluting the solutions to lower the viscosity is unacceptable for, it will also reduce the much sought after high lanthanide concentration of the solution.

SUMMARY OF THE INVENTION

It is thus a major objective of this invention to provide low viscosity, highly concentrated, aqueous solutions of lanthanide salts. In particular, the instant invention provides a low viscosity, water soluble cerium acetate/gluconate composition which when precipitated and pyrolyzed, yields a cerium content in excess of about 10 percent by weight of the original solution.

BRIEF DESCRIPTION OF THE DRAWINGS

FIG. 2 shows the solubility in water (metal content (%) versus temperature (°C.) curves) for i) cerium (+3) acetate; ii) cerium (+3) acetate (1 mol.) and gluconic acid (0.5 mol.); iii) cerium (+3) acetate (1 mol.) and gluconic acid (0.5 mol.) and acetic acid (4.0 mol.); iv) cerium (+3) acetate (1 mol.) and gluconic acid (0.5 mol.) and acetic acid (1.27 mol.).

DETAILED DESCRIPTION OF THE INVENTION

Figure 1:
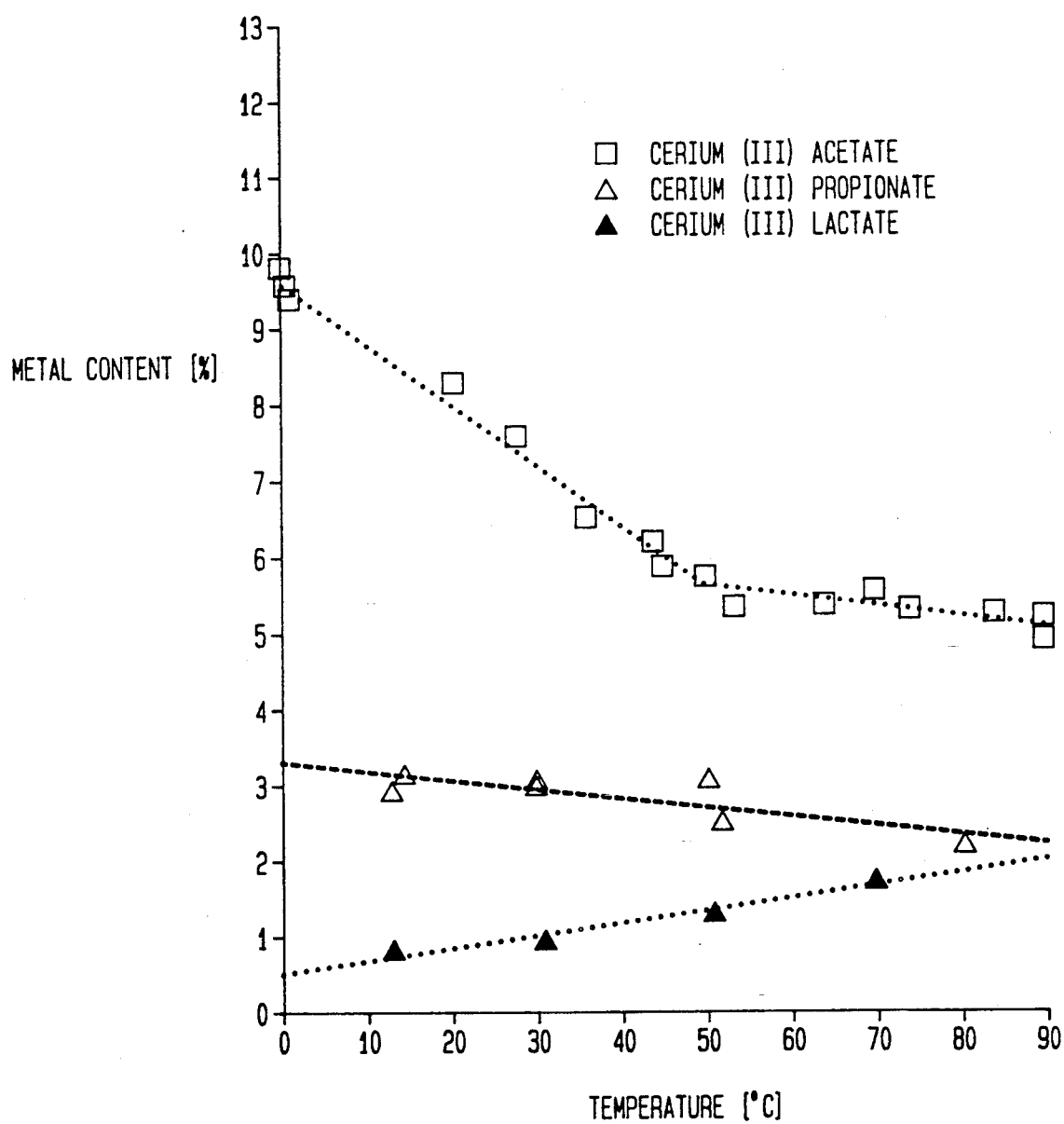
FIG. 1 shows the solubility in water (metal content (%) versus temperature (°C.) curves) for i) cerium (+3) acetate; ii) cerium (+3) propionate; iii) cerium (+3) lactate; and a iv) cerium (+3) acetate (1 mol.) and gluconic acid (0.5 mol.) mixture.

The present invention relates to the discovery that certain lanthanide acetate/lanthanide gluconate salt mixtures are highly soluble in aqueous solutions and that the concentrated solutions possess low viscosities at ambient temperatures. Additionally, by selecting the appropriate amounts of gluconic acid and acetic acid, the solubility of these aqueous salt solutions can be made essentially temperature independent.

The compositions of this invention comprise a lanthanide ion (A) of the lanthanide metals selected from the group consisting of cerium, lanthanum, neodymium and praseodymium; acetic acid (B), and gluconic acid (C) wherein, per mole of A, B is present from about 1.5 to about 8.0 moles and C is present from about 0.3 to about 2.0 moles. Preferably, per mole of A in the compositions, B is present from about 3.0 to about 5.0 moles and C is present from about 0.5 to about 1.0 moles.

Serendipitously, compositions of the instant invention when pyrolyzed, decompose to the oxides with low toxicity emissions, primarily carbon dioxide and water.

Many individual lanthanide acetate salt solutions are commercially available such as cerium acetate or are readily prepared by methods known in the art.

The solutions of the present invention can be prepared by dehydrating an aqueous lanthanide acetate solution and subsequently adding gluconic acid and acetic acid to the resulting solid wherein per mole of lanthanide acetate, the free acetic acid is from about 0 to about 5.0 moles, preferably from about 1.0 to about 4.0 moles and the gluconic acid is from about 0.3 to about 2.0 moles, preferably from about 0.5 to about 1.0 moles. An alternative method is to add acetic acid and gluconic acid together or sequentially to a basic lanthanide salt such as a carbonate in a water slurry wherein per mole of lanthanide carbonate, the acetic acid is from about 1.5 moles to about 8.0 moles, preferably from about 3.0 moles to about 5.0 moles and the gluconic acid is from about 0.3 moles to about 2.0 moles, preferably from about 0.5 moles to about 1.0 moles, preferably at temperatures of from about 25° to about 90° C. and for a time sufficient to ensure completion of the reaction.

Analysis for the lanthanide can be made by any standard method such as pouring the clear salt solution into a tared crucible, gradually heating same until dry enough to insert into a furnace from about 900° to 1000° C. for about one hour; putting in a desiccator to cool and calculating the resulting powder as $CeO_2$.

If the initial solution is cloudy or hazy, the haze is removed by filtration, the filter ashed and the yield calculated as $CeO_2$ loss.

In order to further illustrate the present invention and the advantages thereof, the following specific examples are given, it being understood that same are intended only as illustrative and in nowise limiting.

EXAMPLES 1-4

Solubility limits in water of cerium (+3) lactate, cerium (+3) propionate; cerium (+3) acetate; and cerium (+3) gluconate were determined at from 0° C. to 90° C. and the cerium content (determined by ash) calculated at the solubility limit of the salts at various temperatures within the range. Cerium nitrate was not evaluated for the production of the oxide upon pyrolysis of the nitrate salt yields environmentally undesirable $NO_x$ off-gases. The results are depicted in FIG. 1. Cerium gluconate is not shown for although it was almost infinitely soluble at 25° C., it has a commercially undesirable, relatively high viscosity at useful concentrations. The data illustrate that even at 0° C., the cerium ion content of the water soluble organic salt solutions tested at the solubility limit is less than ten percent and at room temperature, significantly less than eight percent. In fact, under normal shipping conditions, 45° C. is not unexpected and therefore the practically useful concentration of the cerium acetate is actually 6% cerium or less.

EXAMPLES 5-7

A commercially obtained aqueous cerium acetate solution (description) was dried at about $10^{-2}$ Tor. using a vacuum oil pump at from about 40°-50° C. overnight. Solution A was prepared by adding to the cerium acetate sufficient gluconic acid to realize a mole ratio of 0.5 moles of gluconic acid per mole of cerium acetate. Solution B was prepared by adding to the cerium acetate sufficient gluconic acid and acetic acid to realize about 0.5 moles of gluconic acid and 4.0 moles of acetic acid per mole of cerium acetate. Solution C was prepared by adding to the cerium acetate sufficient gluconic acid and acetic acid to realize about 0.5 moles of gluconic acid and 1.27 moles of acetic acid per mole of cerium acetate.

The solubility limits in water of the A, B and C solutions were determined at from 0° to 90° C. and the cerium content (determined by ash) calculated at the solubility limits of the salts at various temperatures within the range.

The results are depicted in FIG. 2.

Solution A comprising the cerium acetate/gluconic acid in a 1:0.5 mol. ratio realizes a low viscosity solution with cerium content in excess of eleven percent over the entire temperature range. Additionally, and most unexpectedly, the addition of free acetic acid, preferably a small amount of free acetic acid as shown in Solution C results not only in a low viscosity water soluble organic cerium salt solution having a cerium metal content in excess of ten percent, but serendipitously, one that is essentially temperature independent from about 0° to 90° C.

EXAMPLE 8

The following illustrates another method of preparing the solutions of the instant invention:

16.02 g (266.78 mmol.) acetic acid was added (at once) to 24 g (68.65 mmol.) cerium carbonate in 30.4 g water in a 250 ml three neck flask equipped with overhead stirrer and thermometer all of which was placed in an oil covered water bath. After six (6) minutes 24.62 g (62.75 mmol.) gluconic acid were added (at once). The reaction mixture was stirred at room temperature (approximately 25° C.) for eight (8) minutes. At this time the $CO_2$ evolution had significantly slowed down. Therefore, the reaction mixture was heated over a period of sixty five (65) minutes to 50° C. After this time the $CO_2$ evolution had stopped and the solution began to clear. It was kept for twenty (20) more hours at 50° C. (After five (5) hours/50° C., no further changes took place.) The final cerium acetate: acetic acid: gluconic acid mol. ratio was 1:3.89:0.91. After this time the light brown reaction mixture was still slightly hazy. It was filtered after cooling to room temperature (4 cm Buchner funnel/#44 filter paper/approximately three and one-half (3.5) hours).

The filter paper was ashed, yielding 17.8 mg $CeO_2$ which is equivalent to 14.49 mg Ce=0.103 mmol. This correlated to a total cerium loss of 0.15%.

Three samples of the filtrate were pyrolyzed in a crucible, yielding 12.93, 12.99 and 12.88% $CeO_2$ (10.53, 10.56 and 10.48Ce).

The theoretical amount of cerium was 10.12%. The actual value was slightly higher (10.53%). This was most likely due to loss of a small amount of water during filtration (vacuum).

EXAMPLE 9

The process of Example 8 was run again wherein the ratio of cerium acetate to acetic acid to gluconic acid was 1:4.26:0.91; the reaction was conducted at 70° C.; and the gluconic acid was added in small increments over a few minutes.

After filtering, the filter paper was ashed, yielding a loss which calculated to be about 0.32%. The filtrate was pyrolyzed in a crucible, yielding 13.08% $CeO_2$ (10.65% Ce).

We claim:

1. A water soluble, organic lanthanide salt composition comprising:
    i) a lanthanide ion (A) of the lanthanide metals selected from the group consisting of cerium, lanthanum, neodymium, and praseodymium;
    ii) acetic acid (B); and
    iii) gluconic acid (C)
    wherein, per mole of A,
       B is from about 1.5 to about 8.0 moles and
       C is from about 0.3 to about 2.0 moles.

2. The composition of claim 1 wherein B is from about 3.0 to about 5.0 moles and C is from about 0.5 to about 1.0 moles.

3. A water soluble, organic cerium salt composition comprising:
    i) cerium ion (A);
    ii) acetic acid (B); and
    iii) gluconic acid (C)
    wherein, per mole of A,
       B is from about 1.5 to about 8.0 moles, and
       C is from about 0.3 to about 2.0 moles.

4. The composition of claim 3 wherein
    B is from about 3.0 to about 5.0 moles, and
    C is from about 0.5 to about 1.0 moles.

5. The process of preparing a water soluble organic lanthanide salt comprising:
    admixing a lanthanide acetate wherein the lanthanide is selected from the group consisting of cerium, lanthanum, neodymium and praseodymium; acetic acid; and gluconic acid wherein per mole of lanthanide acetate, the free acetic acid is from about 0 to about 5.0 moles, and the gluconic acid is from about 0.3 to about 2.0 moles.

6. The process of claim 5 wherein
    the acetic acid is from about 1.0 to about 4.0 moles, and the gluconic acid is from about 0.5 to about 1.0 moles.

7. The process of preparing a water soluble, organic cerium salt composition comprising:
    admixing cerium acetate; acetic acid; and gluconic acid wherein, per mole of cerium acetate, the free acetic acid is from about 0 to about 5.0 moles, and the gluconic acid is from about 0.3 to about 2.0 moles.

8. The process of claim 7 wherein
    the acetic acid is from about 1.0 to about 4.0 moles, and the gluconic acid is from about 0.5 to about 1.0 moles.

9. The process of preparing a water soluble, organic lanthanide salt composition comprising:
    i) preparing an aqueous slurry of a lanthanide carbonate selected from the group consisting of cerium carbonate, lanthanum carbonate, neodymium carbonate and praseodymium carbonate;
    ii) adding to said carbonate slurry simultaneously or sequentially from about 1.5 moles to about 8.0 moles of acetic acid per mole of said lanthanide carbonate and from about 0.3 moles to about 2.0 moles of gluconic acid per mole of said lanthanide carbonate; and
    iii) reacting the mixture of ii) at from about 25° C. to about 90° C.

10. The process of claim 9 wherein
    the acetic acid is from about 3.0 moles to about 5.0 moles, and
    the gluconic acid is from about 0.5 moles to about 1.0 moles.

11. The process of preparing a water soluble, organic cerium salt composition comprising:
    i) preparing an aqueous slurry of cerium carbonate;
    ii) adding to said carbonate slurry, simultaneously or sequentially from about 1.5 moles to about 8.0 moles of acetic acid per mole of cerium carbonate and from about 0.3 moles to about 2.0 moles of gluconic acid per mole of cerium carbonate; and
    iii) reacting the mixture of ii) at from about 25° C. to about 90° C.

12. The process of claim 11 wherein
    the acetic acid is from about 3.0 to about 5.0 moles, and
    the gluconic acid is from about 0.5 to about 1.0 moles.

* * * * *